(12) United States Patent
Hausen et al.

(10) Patent No.: US 8,631,992 B1
(45) Date of Patent: Jan. 21, 2014

(54) FEEDER BELT WITH PADDED STAPLES FOR TRUE MULTI-FIRE SURGICAL STAPLER

(75) Inventors: Bernard A. Hausen, Redwood City, CA (US); Bryan D. Knodel, Flagstaff, AZ (US); Patrick Flanagan, San Diego, CA (US); Bennie Thompson, Cincinnati, OH (US)

(73) Assignee: Cardica, Inc., Redwood City, CA (US)

( * ) Notice: Subject to any disclaimer, the term of this patent is extended or adjusted under 35 U.S.C. 154(b) by 174 days.

(21) Appl. No.: 12/603,521

(22) Filed: Oct. 21, 2009

Related U.S. Application Data

(60) Provisional application No. 61/175,034, filed on May 3, 2009.

(51) Int. Cl.
*A61B 17/10* (2006.01)

(52) U.S. Cl.
USPC .................. 227/179.1; 227/175.1; 227/176.1; 227/181.1; 227/19; 606/219; 606/139; 411/457; 411/920

(58) Field of Classification Search
USPC .............. 227/175.1–182.1, 19; 606/219, 139; 411/457, 920
See application file for complete search history.

(56) References Cited

U.S. PATENT DOCUMENTS

| | | | |
|---|---|---|---|
| 2,127,665 A | 8/1938 | Leslie | |
| 3,086,208 A * | 4/1963 | Eby | 206/339 |
| 3,581,551 A | 6/1971 | Wilkinson | |
| 3,650,453 A | 3/1972 | Smith, Jr. | |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

"Cardica Microcutter Implant Delivery Device 510(k), Cover Sheet, Table 10.1, "Substantial Equivalence Comparison," and Section 12, "Substantial Equivalence Discussion""".

(Continued)

*Primary Examiner* — Michelle Lopez
(74) *Attorney, Agent, or Firm* — Cardica, Inc.

(57) ABSTRACT

An exemplary surgical apparatus may include a feeder belt; at least one staple including a crown fixed to and frangibly separable from the feeder belt, the crown having a first width, and a free end extending from the crown; and at least one pad wider than the first width, wherein each pad is associated with a corresponding crown. An exemplary surgical method using that exemplary apparatus may include placing the feeder belt in proximity to tissue; penetrating the free end of at least one staple into tissue, such that tissue is positioned between the free end and the crown; compressing the free end of at least one staple toward the crown, such that a compressive force is exerted toward the crown; distributing the compressive force across the pad of at least one staple; and shearing at least one staple from the feeder belt. Another exemplary surgical apparatus may include at least one feeder belt having two lateral edges; staples, where each staple includes a first end frangibly connected to a corresponding feeder belt and a second free end; and where the staples form at least one row, each row including at least two staples; and at least one pad, where each pad is located along a corresponding free end of a corresponding staple.

16 Claims, 3 Drawing Sheets

(56) References Cited

U.S. PATENT DOCUMENTS

| | | | |
|---|---|---|---|
| 3,717,294 A | 2/1973 | Green | |
| 3,837,555 A | 9/1974 | Green | |
| 3,899,914 A | 8/1975 | Akiyama | |
| 4,043,504 A | 8/1977 | Hueil et al. | |
| 4,086,926 A | 5/1978 | Green et al. | |
| 4,127,227 A | 11/1978 | Green | |
| 4,228,895 A | 10/1980 | Larkin | |
| 4,275,813 A | 6/1981 | Noiles et al. | |
| 4,317,451 A * | 3/1982 | Cerwin et al. | 606/220 |
| 4,475,679 A | 10/1984 | Fleury, Jr. | |
| 4,523,707 A | 6/1985 | Blake, III et al. | |
| 4,556,058 A | 12/1985 | Green | |
| 4,633,861 A | 1/1987 | Chow et al. | |
| 4,655,222 A | 4/1987 | Florez et al. | |
| 4,719,917 A | 1/1988 | Barrows et al. | |
| 4,762,260 A | 8/1988 | Richards et al. | |
| 4,969,591 A | 11/1990 | Richards et al. | |
| 4,978,049 A | 12/1990 | Green | |
| 5,156,315 A | 10/1992 | Green et al. | |
| 5,170,925 A | 12/1992 | Madden et al. | |
| 5,192,288 A | 3/1993 | Thompson et al. | |
| 5,219,353 A * | 6/1993 | Garvey et al. | 606/157 |
| 5,242,457 A | 9/1993 | Akopov et al. | |
| 5,269,792 A | 12/1993 | Kovac et al. | |
| 5,413,272 A | 5/1995 | Green et al. | |
| 5,415,334 A | 5/1995 | Williamson, IV et al. | |
| 5,456,400 A | 10/1995 | Shichman et al. | |
| 5,476,206 A | 12/1995 | Green | |
| 5,507,776 A * | 4/1996 | Hempel | 606/219 |
| 5,527,319 A | 6/1996 | Green et al. | |
| 5,547,474 A | 8/1996 | Kloeckl et al. | |
| 5,620,289 A | 4/1997 | Curry | |
| 5,620,452 A * | 4/1997 | Yoon | 606/151 |
| 5,626,585 A | 5/1997 | Mittelstadt et al. | |
| 5,630,541 A | 5/1997 | Williamson, IV et al. | |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,833,695 A * | 11/1998 | Yoon | 606/139 |
| 5,855,311 A | 1/1999 | Hamblin et al. | |
| 5,871,135 A | 2/1999 | Williamson, IV et al. | |
| 5,875,538 A | 3/1999 | Kish et al. | |
| 5,894,979 A | 4/1999 | Powell | |
| 5,918,791 A | 7/1999 | Sorrentino et al. | |
| 5,964,774 A | 10/1999 | McKean et al. | |
| 5,993,476 A * | 11/1999 | Groiso | 606/219 |
| 6,264,087 B1 | 7/2001 | Whitman | |
| 6,306,149 B1 | 10/2001 | Meade | |
| 6,391,038 B2 * | 5/2002 | Vargas et al. | 606/153 |
| 6,419,682 B1 | 7/2002 | Appleby et al. | |
| 6,443,973 B1 | 9/2002 | Whitman | |
| 6,592,597 B2 | 7/2003 | Grant et al. | |
| 6,602,252 B2 | 8/2003 | Mollenauer | |
| 6,716,232 B1 | 4/2004 | Vidal et al. | |
| 6,817,508 B1 | 11/2004 | Racenet et al. | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,111,768 B2 | 9/2006 | Cummins et al. | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,258,262 B2 | 8/2007 | Mastri et al. | |
| 7,401,720 B1 | 7/2008 | Durrani | |
| 7,434,715 B2 | 10/2008 | Shelton, IV et al. | |
| 7,467,740 B2 | 12/2008 | Shelton, IV et al. | |
| 7,497,865 B2 | 3/2009 | Willis et al. | |
| 7,506,791 B2 | 3/2009 | Omaits et al. | |
| 7,517,356 B2 | 4/2009 | Heinrich | |
| 7,588,177 B2 | 9/2009 | Racenet | |
| 7,604,151 B2 | 10/2009 | Hess et al. | |
| 7,635,073 B2 | 12/2009 | Heinrich | |
| 7,635,373 B2 | 12/2009 | Ortiz | |
| 7,641,432 B2 | 1/2010 | Lat et al. | |
| 7,644,848 B2 | 1/2010 | Swayze et al. | |
| 7,735,703 B2 * | 6/2010 | Morgan et al. | 227/176.1 |
| 7,918,873 B2 * | 4/2011 | Cummins | 606/219 |
| 2003/0120284 A1 | 6/2003 | Palacios et al. | |
| 2003/0236551 A1 | 12/2003 | Peterson | |
| 2004/0028502 A1 * | 2/2004 | Cummins | 411/457 |
| 2005/0184121 A1 | 8/2005 | Heinrich | |
| 2005/0267530 A1 * | 12/2005 | Cummins | 606/219 |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2006/0241660 A1 | 10/2006 | Bombard et al. | |
| 2006/0253143 A1 | 11/2006 | Edoga | |
| 2006/0291981 A1 * | 12/2006 | Viola et al. | 411/457 |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2008/0078807 A1 | 4/2008 | Hess et al. | |
| 2008/0172088 A1 * | 7/2008 | Smith et al. | 606/219 |
| 2008/0272175 A1 | 11/2008 | Holsten et al. | |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Gong, Shao W., "Perfectly flexible mechanism and integrated mechanism system design", *Mechanism and Machine Theory* 39 (2004), (Nov. 2004),1155-1174.

Lim, Jonas J., et al., "A review of mechanism used in laparoscopic surgical instruments", *Mechanism and Machine Theory* 38, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

\* cited by examiner

FEEDER BELT WITH PADDED STAPLES FOR TRUE MULTI-FIRE SURGICAL STAPLER

This application claims priority to U.S. Provisional Patent Application Ser. No. 61/175,034, filed on May 3, 2009, which is hereby incorporated by reference in its entirety.

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter.

In order to overcome these difficulties, Cardica, Inc. of Redwood City, Calif. has developed a true multi-fire endocutter that is capable of firing multiple times without the need to utilize single-use-cartridges. That endocutter is described in, for example, U.S. patent application Ser. No. 12/263,171, filed on Oct. 31, 2008 (the "Endocutter Application"), which is hereby incorporated by reference in its entirety. Referring to FIG. 1, the Endocutter Application, among other items, discloses a feeder belt 2 to which a plurality of staples 4 are frangibly attached. Because the staples 4 are fixed to and frangibly separated from the feeder belt 2, the staples 4 can be small, facilitating the use of such staples 4 in minimally-invasive surgery. However, a disadvantage of small staples 4 can be the "cheese-wire effect," in which a thin staple cuts through damaged or diseased tissue rather than holding that tissue.

BRIEF DESCRIPTION OF THE DRAWINGS

The use of the same reference symbols in different figures indicates similar or identical items.

DETAILED DESCRIPTION

Figure 1:
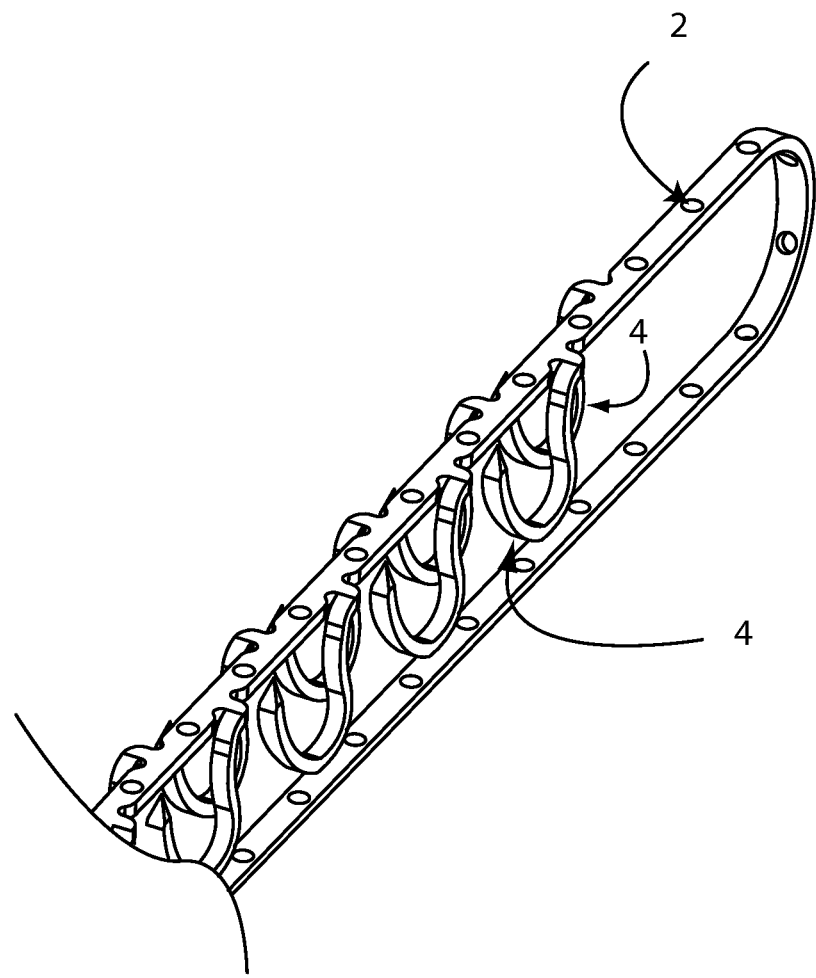
FIG. 1 is a perspective view of a feeder felt to which a plurality of staples are frangibly attached.
Figure 2:
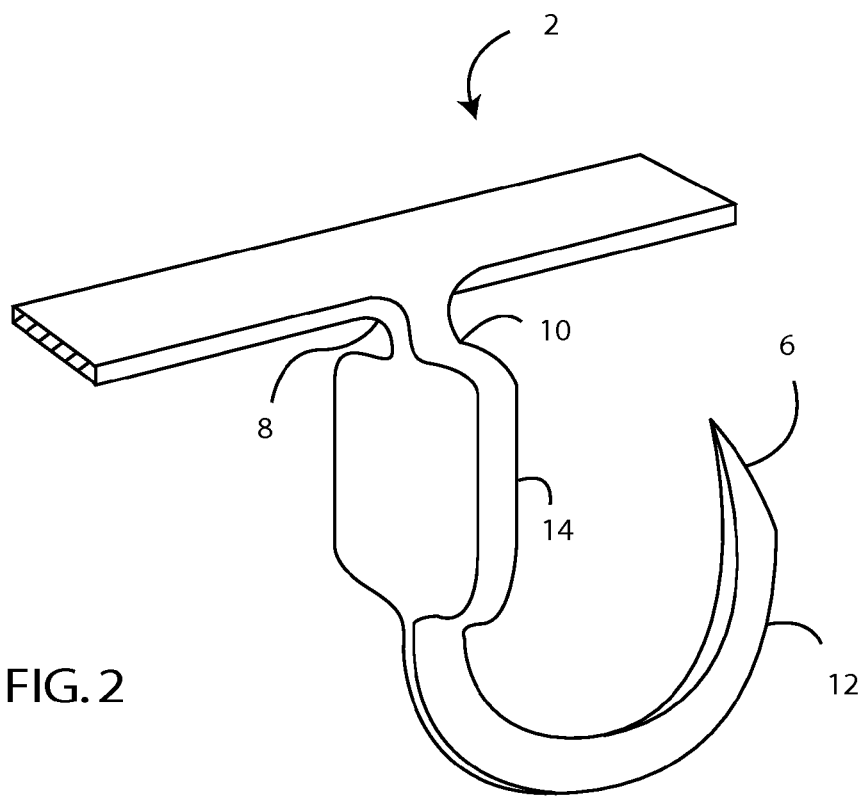
FIG. 2 is a perspective view of an exemplary padded staple frangibly attached to a feeder belt.
Figure 3:
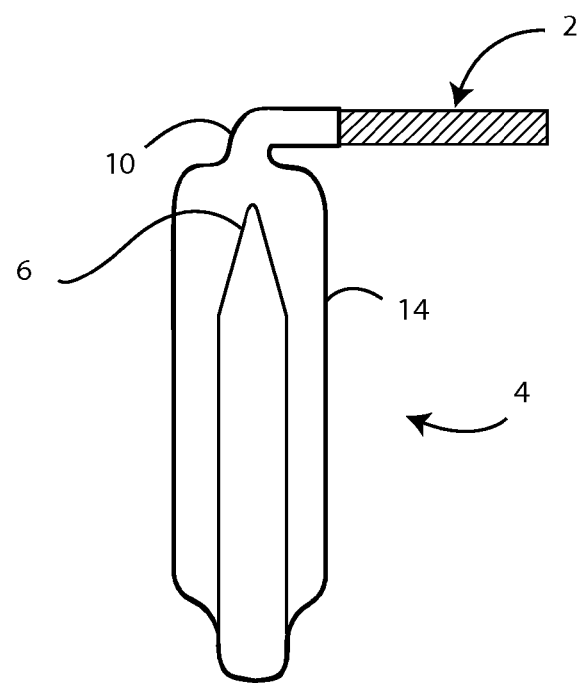
FIG. 3 is an end view of the exemplary staple of FIG. 2.
Figure 4:
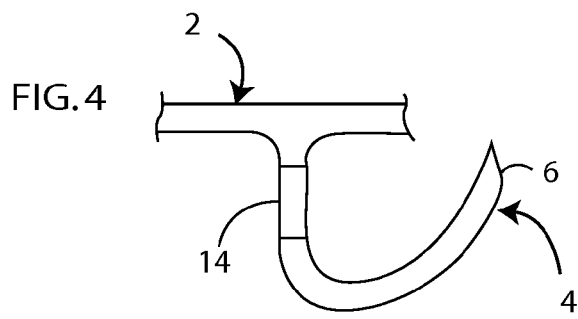
FIG. 4 is a side view of the exemplary staple of FIG. 2.

Referring to FIGS. 2-4, a single staple 4 is shown for clarity, along with a portion of the feeder belt 2 to which that staple 4 is frangibly attached. Multiple staples 4 are attached to the feeder belt 2 as described in the Endocutter Application, and all or a portion of those staples 4 may be configured as the staple 4 of FIGS. 2-4. The staple 4 includes a free tissue-penetrating end 6, and an opposite end 8 frangibly connected to the feeder belt 2. The portion of the staple 4 closer to the end 8 connected to the feeder belt 2 may be referred to as the crown 10, and the portion of the staple 4 closer to the free end 6 may be referred to as the tine 12, solely for convenience in describing the structure of the staple 4. A pad 14 may be connected to the crown 10 in any suitable manner. Advantageously, the pad 14 is fabricated integrally with the remainder of the staple 4, which is advantageously fabricated integrally with the feeder belt 2. However, the pad 14 may be fabricated separately from the staple 4 and attached to the staple 4 in any suitable manner, such as by welding, adhesive or any other suitable method, mechanism or structure. The pad 14 may have any suitable shape. As one example, the pad 14 may be generally rectangular. As another example, the pad 14 may be generally oval in shape. The pad 14 may simply be a wide area of the crown 10, wider than a remainder of the crown 10. The width of the pad 14 distributes compressive force across a larger cross-sectional area of tissue than the crown 10 could. During firing of the staple 4, the free end 6 of the staple 4 is compressed toward the crown 10 in order to engage tissue. Where a pad 14 is provided, the compressive force between the crown 10 and the free end 6 of the staple 4 is distributed laterally across the entire pad 14, rather than being limited to the width of the crown 10 alone. By distributing compressive force across a larger area, any cheese-wire effect during or subsequent to staple formation is minimized.

Figure 5:
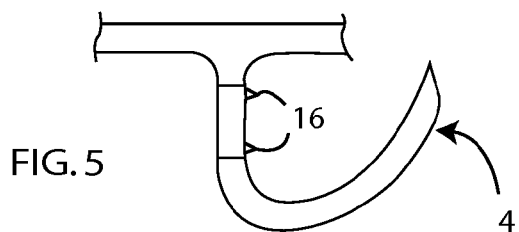
FIG. 5 is a side view of another exemplary padded staple, including spikes extending therefrom.
Figure 6:
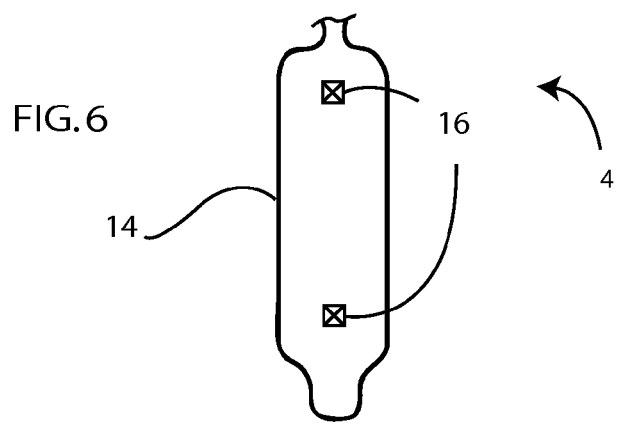
FIG. 6 is an end view of the exemplary staple of FIG. 5.

Optionally, referring also to FIG. 5, the pad 14 may include one or more protrusion 16 projecting therefrom. Any number of protrusions 16 may be utilized. The protrusions 16 may extend from any suitable location or locations on the pad 14, and in any suitable direction. The protrusions 16 may be sharp spikes in one embodiment. Alternately, at least one protrusion 16 may be blunt. As one example, the protrusions 16 may extend from the lateral center of the pad 14 in the direction toward the free end 6 of the staple 4, as shown in FIG. 5. Alternately, one or more protrusions 16 may extend laterally outward from the pad 14 and then bend toward in the direction toward the free end 6 of the staple 4. The protrusion or protrusions 16, where utilized, may provide additional holding power for the staple 4 in tissue. Further, the protrusion or protrusions 16 may assist in holding tissue across the entire width of the pad 14 to assist in distributing the tissue compressive force during and after deployment across the entire pad 14. Further, the protrusion or protrusions 16 may counter any rotation of the staple 4 in tissue after deployment, by providing one or more additional points of engagement with tissue.

Figure 7:
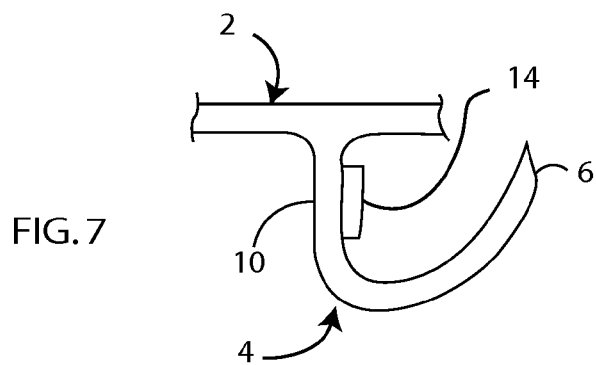
FIG. 7 is a side view of another exemplary padded staple.

Alternately, referring to FIG. 7, the pad 14 may be positioned on top of the crown 10, thereby adding thickness as well as width to the crown 10. Such a pad 14 may be fabricated integrally with the staple 4. However, the pad 14 may be fabricated separately from the staple 4 and attached to the staple 4 in any suitable manner. The pad 14 may be fabricated from the same material as the staple 4, or a different material. Where the pad 14 is fabricated from a different, softer material than the staple 4, the pad 14 may act as a buttress, and may be fabricated from any suitable staple buttress material. Advantageously, the pad 14 is wider than the crown 10. The pad 14 may be resorbable, if desired. The pad 14 may be fabricated from any suitable material, such as (but not limited to) VICRYL®, produced by Ethicon, Inc. of Somerville N.J.; DEXON®, produced by Sherwood-Davis and Geck of St. Louis, Mo.; TEFLON®, produced by E. I. DuPont de Nemours & Co. of Wilmington, Del.; GORE-TEX®, produced by W.L. Gore of Flagstaff, Ariz.; animal material such as tanned bovine pericardium; biocompatable elastomers such as ε-caprolactone glycolide; stainless steel, nickel-titanium alloy or other metal; or polymers, whether resorbable or not.

Alternately, the free end 6 of the staple 4 may include one of the embodiments of the pad 14 described above, or a different embodiment of a pad 14. The free end 6 of the staple 4 may include a pad 14 instead of the crown 10 including a pad 14. Alternately, both the free end 6 and the crown 10 of the staple 4 may include a pad 14. Where both the crown 10 and the free end 6 of the staple 4 include a pad 14, distribution of compressive force in tissue may be enhanced further.

What is claimed is:

1. A surgical apparatus, comprising:
a feeder belt, wherein a horizontal surface of said feeder belt lies substantially in a first plane;
at least one staple integral with and frangibly separable from said feeder belt, wherein said at least one staple comprises:
a single tissue-penetrating end;
an opposite end frangibly connected to said feeder belt;
a crown extending from said opposite end and having a first width; and
at least one pad integral with said crown and having a second width that is wider than said first width, and wherein a second plane defined through the single tissue penetrating end and the crown is substantially orthogonal to the first plane.

2. The apparatus of claim 1, wherein said at least one pad comprises an area of said crown having said second width.

3. The apparatus of claim 1, wherein said at least one pad is generally rectangular.

4. The apparatus of claim 1, further comprising at least one protrusion extending from said at least one pad.

5. The apparatus of claim 4, wherein said at least one protrusion is a spike.

6. The apparatus of claim 4, wherein said at least one protrusion is substantially perpendicular to said pad.

7. The apparatus of claim 1, wherein said at least one pad is positioned on top of said crown.

8. The apparatus of claim 1, further comprising at least one additional pad on said staple nearer said single end than said opposite end.

9. The apparatus of claim 1, wherein said at least one staple extends below a bottom surface of a lateral edge of said feeder belt.

10. The apparatus of claim 1, wherein the feeder belt forms a continuous loop.

11. The apparatus of claim 1, wherein said at least one staple is generally U-shaped.

12. A surgical apparatus, comprising:
at least one feeder belt comprising two lateral edges and a horizontal surface between the lateral edges, wherein the horizontal surface lies substantially in a first plane;
a plurality of staples, wherein each of said plurality of staples has a first width and comprises:
a first end frangibly connected to said at least one feeder belt
a single second tissue penetrating end; and
at least one pad integral with said staple and having a second width that is greater than said first width;
wherein a longitudinal axis of said at least one staple lies substantially in a second plane that is substantially orthogonal to said first plane, and
wherein said plurality of staples forms at least one row including at least two said staples.

13. The apparatus of claim 12 wherein said at least one pad comprises an area of said staple wider than a remainder thereof.

14. The apparatus of claim 12, wherein said at least one pad is positioned on a crown of each of said plurality of staples, wherein said crown extends from said first end.

15. The apparatus of claim 12, wherein said single second end of each said staple is located proximal to said first end thereof.

16. A surgical method for treating tissue, comprising:
providing a feeder belt coupled with at least one staple, wherein horizontal surface of the feeder belt lies substantially in a first plane, and wherein each of said at least one staple comprises:
a first end integral with and frangibly separable from said feeder belt;
a crown extending from the first end, said crown having a first width;
a single second, free, tissue-penetrating end extending from said crown, wherein a longitudinal axis of said at least one staple lies substantially in a second plane that that is substantially orthogonal to said first plane; and
a pad integral with said crown, wherein said pad is wider than said first width;
placing said feeder belt in proximity to tissue;
penetrating said free end of said at least one staple into tissue, such that tissue is positioned between said free end and said crown;
compressing said free end of at least one said staple toward said crown by slidably advancing a wedge laterally under the feeder belt, such that a compressive force is exerted toward said crown;
distributing said compressive force across said pad of at said least one staple; and
shearing said least one from said feeder belt.

* * * * *